United States Patent
Kendig et al.

(10) Patent No.: US 9,180,218 B2
(45) Date of Patent: Nov. 10, 2015

(54) SELF DECONTAMINATING SYSTEM AND FABRIC

(75) Inventors: Martin W. Kendig, Thousand Oaks, CA (US); Young J. Chung, Calabasas, CA (US)

(73) Assignee: Teledyne Scientific & Imaging, LLC, Thousand Oaks, CA (US)

(*) Notice: Subject to any disclaimer, the term of this patent is extended or adjusted under 35 U.S.C. 154(b) by 1440 days.

(21) Appl. No.: 11/415,662

(22) Filed: May 1, 2006

(65) Prior Publication Data
US 2010/0047124 A1 Feb. 25, 2010

Related U.S. Application Data

(63) Continuation-in-part of application No. 11/241,518, filed on Sep. 30, 2005.

(51) Int. Cl.
| | |
|---|---|
| C25B 9/00 | (2006.01) |
| C25B 15/00 | (2006.01) |
| C25D 17/00 | (2006.01) |
| C25C 7/00 | (2006.01) |
| C25C 7/02 | (2006.01) |
| A61L 2/232 | (2006.01) |
| A62D 3/115 | (2007.01) |
| A62D 5/00 | (2006.01) |
| C01B 7/14 | (2006.01) |
| C23C 8/02 | (2006.01) |
| C23C 26/00 | (2006.01) |
| C23C 30/00 | (2006.01) |

(52) U.S. Cl.
CPC .............. *A61L 2/232* (2013.01); *A62D 3/115* (2013.01); *A62D 5/00* (2013.01); *C01B 7/14* (2013.01); *C23C 8/02* (2013.01); *C23C 26/00* (2013.01); *C23C 30/00* (2013.01)

(58) Field of Classification Search
CPC .......... C25B 9/00; C25B 15/00; C25D 17/00; C25C 7/00; C25C 7/02
USPC .......................... 204/242, 193, 194, 410, 421
See application file for complete search history.

(56) References Cited

U.S. PATENT DOCUMENTS

| | | | | |
|---|---|---|---|---|
| 2,643,222 | A | * | 6/1953 | Cox .............................. 205/706 |
| 4,019,508 | A | | 4/1977 | Der Estephanian et al. ......................... 128/142.7 |

(Continued)

FOREIGN PATENT DOCUMENTS

WO  WO 02/00267  *  3/2002  ................ A61L 9/00

OTHER PUBLICATIONS

US 2002/0134051 A1; Kurth; Sep. 26, 2002.
(Continued)

*Primary Examiner* — Zulmariam Mendez
(74) *Attorney, Agent, or Firm* — Koppel, Patrick, Heybl & Philpott

(57) ABSTRACT

A self-decontaminating system for decontaminating a surface on demand is disclosed herein. The system contains an electrochemical cell and at least one portion of the surface forms a functional component of the cell. The system may include an electrocatalytic fabric which is flexible and resistant to tears and breaks, such that the fabric can be rolled up or pleated in order to provide a high surface area structure that can serve as an active filter. The fabric can function as a stand-alone system or a protective coating. Also disclosed are methods for fabricating, decontaminating, and regenerating the self-decontaminating fabric.

20 Claims, 2 Drawing Sheets

(56) References Cited

U.S. PATENT DOCUMENTS

| | | | |
|---|---|---|---|
| 4,061,557 A | 12/1977 | Nishizawa et al. | 204/277 |
| 4,730,551 A | 3/1988 | Peludat | 98/315 |
| 5,322,533 A | 6/1994 | Todorovic | 55/385.2 |
| 5,405,434 A * | 4/1995 | Inculet | 96/54 |
| 5,713,137 A | 2/1998 | Fujita | 34/106 |
| 5,814,204 A * | 9/1998 | D'Muhala | 205/705 |
| 6,030,519 A | 2/2000 | Keller et al. | 205/705 |
| 6,245,132 B1 | 6/2001 | Feldman et al. | 96/28 |
| 6,315,886 B1 * | 11/2001 | Zappi et al. | 205/701 |
| 6,482,309 B1 | 11/2002 | Green et al. | 205/619 |
| 6,797,044 B2 | 9/2004 | Ou Yang et al. | 96/224 |
| 7,993,495 B2 | 8/2011 | Kinlen et al. | 204/175 |
| 8,419,913 B2 | 4/2013 | Sato et al. | 204/403.04 |
| 2007/0141434 A1 | 6/2007 | Joshi | |

OTHER PUBLICATIONS

US 2004/0081596 A1; Hsi; Apr. 29, 2004.
US 2004/0103790 A1; Yang et al.; Jun. 3, 2004.
US 2004/0147214 A1; Oono; Jul. 29, 2004.
US 2005/0186108 A1; Fields; Aug. 25, 2005.
US 2005/0207951 A1; Lee et al.; Sep. 22, 2005.
US 2005/0257609 A1; Lin; Nov. 24, 2005.
Chemical/Biological Sensing and Decontamination. Technology Description [online]. Triton Systems, Inc. [retrieved on Apr. 14, 2006]. Retrieved from the Internet: <URL: http://www.tritonsys.com/technologies/chembio.htm>.

* cited by examiner

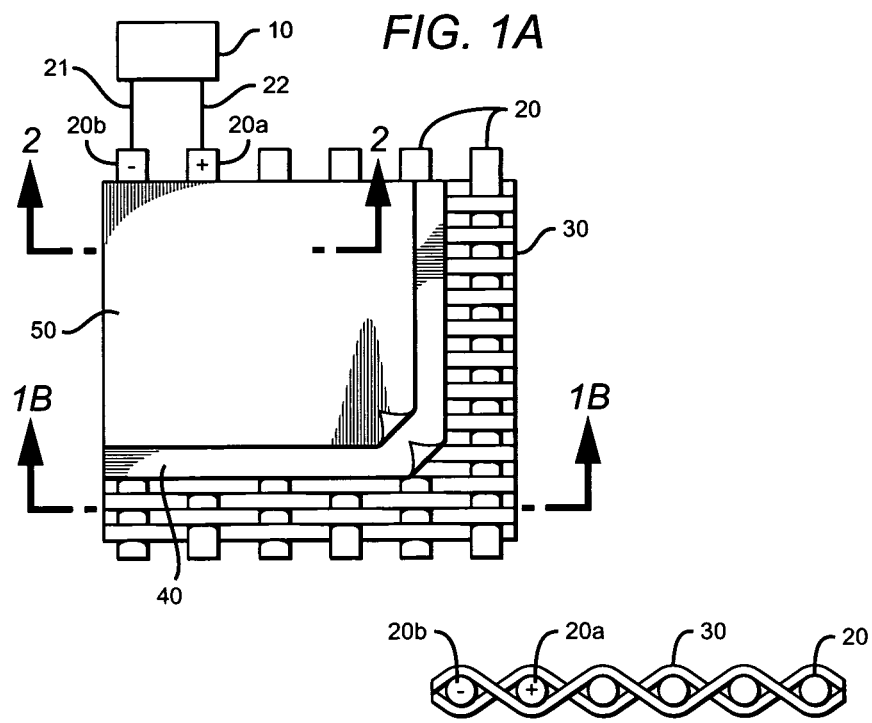
FIG. 1A
FIG. 1B
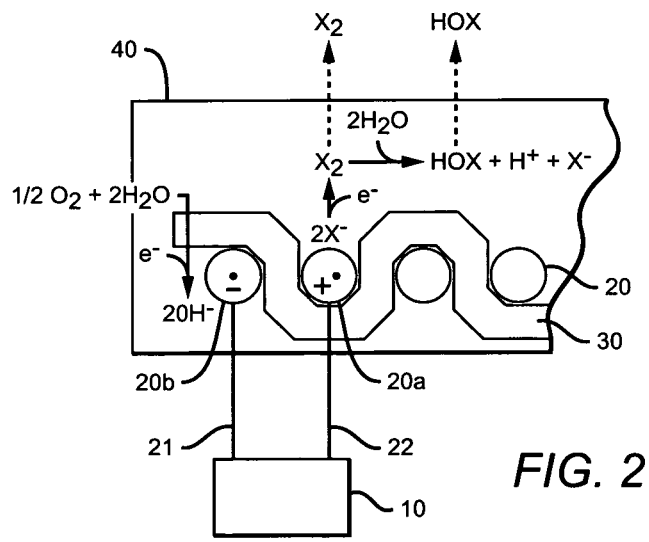
FIG. 2

SELF DECONTAMINATING SYSTEM AND FABRIC

CROSS REFERENCE TO RELATED APPLICATION

This application is a continuation-in-part of U.S. application Ser. No. 11/241,518 filed on Sep. 30, 2005.

STATEMENT AS TO FEDERALLY SPONSORED RESEARCH

This invention was made with Government support under Grant No. DARPA 71247 0006 awarded by the Defense Advanced Research Projects Agency (DARPA). The federal government may have certain rights in the invention.

BACKGROUND OF THE INVENTION

1. Field of the Invention

The invention relates in general to a non-destructive, electrically-activated, self-decontaminating system for decontaminating a surface and a self-decontaminating fabric which incorporates such a system.

2. Description of the Related Art

After exposure to hazardous chemical or biological agents, the surface of a contaminated object located in a battle field, or in a remote area subjected to an accidental release of hazardous materials, is generally difficult to decontaminate. The availability of decontamination systems at or near such sites is usually limited or non-existent and, in particular, the use of an external decontamination system may be difficult or impractical in a situation where a soldier or relief worker must enter an area on foot and therefore bear the weight or bulkiness of such additional items as well as the responsibility of ensuring they arrive intact. In addition, it may be difficult to regenerate the active ingredients of a decontamination system under such conditions if they become depleted.

It may also be difficult to physically access the surface of an object in order to decontaminate it, regardless of location, particularly electronics enclosed within or behind a protecting structure. Furthermore, many decontaminating agents are delivered as aqueous solutions which can be detrimental to the functionality of the device being treated, particularly those containing water-sensitive electronic components.

Health, safety, or environmental concerns may also be an issue. The nature of a surface such as human skin or clothing, for example, may not be amenable to decontamination by the systems available on site, and decontamination of objects used in facilities open to the public or located in residential or environmentally sensitive areas can be similarly difficult to treat with existing systems.

Various systems and compositions have been proposed in the past to neutralize surfaces contaminated by hazardous biological or chemical agents, including coatings of monomeric or polymeric compositions delivered as foams, sprays, liquids, fogs, aerosols, and photoactive compositions that generate ozone when irradiated with ultraviolet (UV) light. In addition, several types of activated ion exchange resins in the form of dry aerosols, dust coatings, or admixed with a carrier (to form a coating) have been used to decontaminate surfaces, and activated resin can also be used to decontaminate fluids. Furthermore, electron beam irradiation, high field ionization, and UV irradiation can be used to decontaminate surfaces.

However, each of these references suffers from one or more of the following disadvantages: the supply and transport of equipment such as UV lamps to a contaminated site would be impractical or impossible; the active ingredients are external and must be placed in physical contact with the contaminated surface of the object in order to decontaminate it; the composition or resin is active once applied but can not be activated on demand; the active ingredients are difficult to regenerate if depleted; the systems or coatings used for decontamination are inflexible or not resistant to tears or breaks; the solvents or carriers used to deposit the active ingredients are detrimental to the functionality of the object or device being treated; the technique requires an enclosed space, heavy or bulky equipment, or is too costly for remote or general applications; or activation of the system is hazardous to the environment or to human health or safety.

SUMMARY OF THE INVENTION

The present invention is directed to a non-destructive, electrically-activated, self-decontaminating system for decontaminating a surface where at least one portion of the surface is integrated into the system and forms a functional component of an electrochemical cell.

The system can be activated on demand and readily regenerated after activation and depletion. In one embodiment of the invention, activation of the system releases an oxidizing agent effective in deactivating chemically or biologically active agents at or near the surface.

The invention also provides a self-decontaminating fabric incorporating the system which can render chemical and biological agents non-hazardous while remaining flexible and resisting tears and breaks, as well as methods for fabricating, decontaminating, and regenerating the fabric. The fabric can be rolled up or pleated to provide a high surface area structure which can serve as an active filter.

The fabric can be lightweight, easily mass produced by existing technologies, and readily incorporated into clothing or equipment as either a stand-alone system or a protective coating. Therefore, the fabric can be used for many purposes in both local and remote locations including, without limitation, protective clothing, air-filtration media, shelter, or protective coatings.

BRIEF DESCRIPTION OF THE DRAWINGS

FIG. 1A is a schematic top view of a self-decontaminating woven fabric incorporating features of the invention. The fabric includes a single layer of alternating conducting and non-conducting tows in contact with electrolyte.

FIG. 1B is a schematic transverse cross section view through the fabric of FIG. 1A showing the insulating and conducting tow arrangement in the fabric.

FIG. 2 is a schematic transverse cross section view through one insulating tow in FIG. 1A showing the chemical reactions induced by activating a self-decontaminating woven fabric incorporating features of the invention.

DETAILED DESCRIPTION OF THE INVENTION

Figure 3:
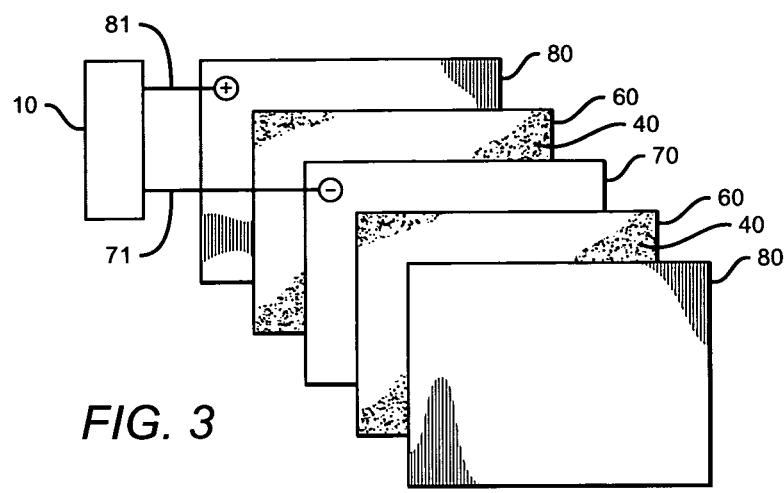
FIG. 3 is a schematic perspective view of a multilayer electrochemical cell incorporating features of the invention. The cell includes three conducting layers in contact with electrolyte.

The present invention relates generally to a non-destructive, electrically-activated, self-decontaminating system for decontaminating a surface by releasing, on demand, an oxidizing agent effective in deactivating certain chemically or biologically active agents at or near the surface, and which can be readily regenerated after activation and depletion. The invention also provides a self-decontaminating fabric incorporating the system which can render chemical and biological agents non-hazardous while remaining flexible and resisting tears and breaks, as well as methods for fabricating, decontaminating, and regenerating the fabric and use of the fabric as a self-decontaminating coating.

Other features and advantages of the invention will be apparent from the following detailed description when taken together with the drawings, and from the claims. The following description presents preferred embodiments of the invention representing the best mode contemplated for practicing the invention. This description is not to be taken in a limiting sense but is made merely for the purpose of describing the general principles of the invention whose scope is defined by the appended claims.

Before addressing details of embodiments described below, some terms are defined or clarified. As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of the "a" or "an" are employed to describe elements and components of the invention. This is done merely for convenience and to give a general sense of the invention. This description should be read to include one or at least one and the singular also includes the plural unless it is obvious that it is meant otherwise.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

As used herein, the term "adjacent to" when referring to a layer or coating on a surface, does not necessarily mean that the coating is immediately next to the surface; there may or may not be another contiguous or noncontiguous layer or material present between the layer or coating and the surface.

As used herein, the term "adjoining atmosphere" is intended to mean the atmosphere which lies next to or in contact with the surface.

As used herein, the term "biological agent" refers to hazardous biological organisms including without limitation viruses, bacteria, and parasites in any form as well as biologically generated toxins.

As used herein, the term "carbon tow" is intended to mean a tow composed at least in part of conducting filaments or fibers whose elemental composition includes carbon.

As used herein, the term "chemical agent" is intended to mean a hazardous chemical compound including without limitation chemical warfare agents and hazardous industrial compounds As used herein, the terms "deposit", "depositing" or "deposited" when referring to electrolyte deposition is intended to mean any standard means for deposition which does not affect the activity of the electrolyte, including without limitation brushing, rolling, spraying, pouring, spin coating, dip coating, and ink jet printing. A coating or layer thus formed may have various types of structures or characteristics including without limitation coatings which are uniform, patterned, contiguous, noncontiguous, surface-layered or embedded. Furthermore, the depth of electrolyte penetration on or after deposition may vary depending upon the nature of the electrolyte, substrate (e.g. fabric), or process used, such that the resulting substrates can be, without limitation, filled, covered, or impregnated with electrolyte.

As used herein, the term "decontaminate" or "decontaminating" when referring to a surface is intended to mean devitalizing or ridding part or all the surface of contamination after exposure to one or more toxic agents, including without limitation chemical or biological agents.

As used herein, the term "devitalize" when used to describe a biological or chemical agent is intended to mean that the agent is destroyed, rendered totally inactive, or made substantially less effective. An agent may be devitalized in a number of ways including, without limitation, oxidation, disinfection or decomposition.

As used herein, the term "dimensionally stable" when referring to tows is intended to mean the tow retains its dimensional properties under electrolysis, including without limitation its shape, size, thickness, and width.

As used herein, the term "electrochemical cell" is intended to mean an electrochemical system comprising at least one anode and at least one cathode in mutual contact with at least one electrolyte.

As used herein, the term "insulating tows" is intended to mean a tow composed at least in part of non-conducting fibers.

As used herein, the term "on demand" when referring to activation of a decontamination system is intended to mean that the system can be activated or deactivated at will, including without limitation continual activation, activation at or shortly after the time of exposure to contamination, or deactivation following a period of time after exposure.

As used herein, the term "self-decontaminating coating" when referring to a layer or fabric adjacent to a surface is intended to mean a self-decontaminating layer or fabric which, when activated, can decontaminate the adjacent surface.

As used herein, the term "surface" when referring to the surface of an object is intended to mean the exterior or upper boundary of an object or body including the adjoining atmosphere.

As used herein, the term "tow" is intended to mean a bundle of continuous filaments. A carbon tow may be a collection of one or more individual carbon filaments bundled into a fiber or thread. Carbon tows can be composed of one or more conducting fibers or filaments and insulating tows can be composed of one or more non-conducting filaments or fibers.

Attention is now directed to more specific details of embodiments that illustrate but not limit the invention.

FIGS. 1A and 1B are schematic diagrams of one embodiment of the present invention, a self-decontaminating fabric which, in conjunction with an external power source (10), can form a flexible electrochemical cell. The fabric can be lightweight, easily produced by existing technologies including without limitation, weaving or knitting, and be readily incorporated into clothing or equipment.

The fabric shown in FIGS. 1A and 1B consists of conducting carbon tows (20) woven together with alternating non-conducting tows (30) to electrically isolate (separate) the conducting tows (20); a cross section of the alternating tow arrangement is shown in FIG. 1B. The conducting tows (20) and non-conducting tows (30) in the woven structure are filled, covered, or impregnated with solid, semi-solid, or gel electrolyte (40) that provides paths of ionic conductivity between the conducting tows (20). This embodiment is flexible and can be easily rolled up or pleated to form an active filter.

The electrolyte can be a non-hydroscopic solid, semi-solid gel, or matrix which includes a liquid entrapped therein, the layer being ionically conducting but electrically non-conducting. Electrolytes such as ethylene carbonate and propylene carbonate, for example can easily set or solidify into gels without external manipulation. The ionic characteristics of the electrolyte can be provided by chemical compounds which can release an ionizing reagent, such as a halide salt that can release a halogen anion (I—, Cl—, Fl— or BR—) once activated. The matrix of the electrolyte should be electrically non-conducting (electrically insulating), hydrophobic, and chemically stable in the presence of the generated oxidant. Polyethylene oxide, Nafion (a perfluorinated polymer) and crystalline RbAg4I5 are non-limiting examples of suitable solid electrolytes. Examples of suitable ionic semi-liquid gel electrolytes include without limitation quaternary alkyl ammonium in alky carbonate/polyacrylonitrile (PAN) gels with organic solvents, materials used in dye sensitive solar cells or electrochromic glass, and sol-gels derived from porous silica gels such as Ormolyte, which is formed from tetraethyl orthosilicate (TEOS) and polyethylene glycol (PED) doped with ionic liquid containing a halide salt.

The electrolyte (40) can also contain a precursor to an active oxidant, preferably a halide anion which can be converted to zero valent iodine or high valent halo-acids via electrolysis at a positively charged tow (20a). Suitable precursors include but are not limited to quaternary ammonium halide salts that dissolve as mobile ions in the gel. Electrolyte compositions incorporating oxidizing agent precursors can be applied to (deposited on) the fabric by any suitable means, including without limitation brushing, rolling spraying, printing, or pouring. The composition may be applied either directly or admixed with a suitable carrier such as a paint-type carrier coating such as a water- or organic solvent-based carrier, or a polymeric material.

Electrolyte (40) impregnated into the fabric provides a reservoir for the precursor and good ionic conduction between conducting tows (20) while allowing part of the surface of the tow to be exposed in order to facilitate the release of the electrolytically-generated oxidant. Alternatively, the gel could partially cover or provide a thin, contiguous cover or layer on top of the fabric as shown in FIG. 1A, as long as oxidant generated at the surface of the fiber can readily diffuse from the tow to the surface of the fabric where it provides its disinfecting role.

The fabric surface may be covered with one or more additional cloth layers (50) that provide additional protection against contaminants by, for example, rendering the surface hydrophilic or hydrophobic, or presenting materials useful for mediating the destruction of spores, including without limitation sporocides and germinant inhibitors. Such layers could be used to target specific agents like, for example, *Bacillus anthracis* which begins its infectious cycle as a metabolically dormant endospore that initiates anthrax by entering a host and then rapidly differentiating into vegetative bacilli through the process of germination.

The conducting warp tows (20), non-conducting weft tows (30), and electrolyte (40) of the fabric can form an electrochemical cell when connected via leads (21) and (22) to the respective poles of a switched (i.e. on-off) power source (10). Application of a potential bias between alternating tows using the external power source (10) can make the alternating conducting tows either positive (anodes) or negative (cathodes) and create an electron flow through the cell. The electron flow can then produce the oxidant at the anode, which in turn can chemically oxidize and deactivate the contaminating agent at or near the surface. The decomposition/generation rate of the oxidant is dependent on the level (amount) of current applied and the direction of current flow (i.e. the greater the current applied, the greater the flow of oxidant generated). A typical power source for the invention provides 5V at 1-10 μamp/$cm^2$.

Alternatively, the electrochemical cell could be photo-activated (i.e. photocell, solar radiation), causing electrons to flow when exposed to light. The system could also include one or more sensors capable of detecting a chemical or biological agent which, upon exposure to that agent, could activate the power source or a shunt causing current to flow through the electrochemical cell structure.

FIG. 2 shows a transverse cross section of the fabric shown in FIG. 1A taken through one insulating tow (30), and a schematic representation of the oxidative conversion of a halide anion to a zero valent (elemental) halogen. For simplicity, the additional surface layer (50) shown in FIG. 1A has been excluded and the conducting tows (20) and non-conducting tows (30) are shown as being immersed in electrolyte (40). Similarly, although the external power source (10) in FIG. 2 is shown to contact only two tows, in practice it contacts every conducting tow with alternating polarity.

The ionically conducting gel electrolyte shown in FIG. 2 contains a precursor halide ion $X^-$. $X^-$ could be any one of the halides, including without limitation chloride ($Cl^-$), bromide ($Br^-$), or iodide ($I^-$). Application of a potential bias between the alternating conducting tows of the fabric shown in FIG. 1 using an external power source (10) makes the alternating tows either positively charged anodes (20*a*) or negatively charged cathodes (20*b*). Once activated, electrons flowing from the power source connected to the electrochemical cell cause oxidation of nearby halide ions ($2X^-$) in the electrolyte at the anode to a zero valent oxidizing species, elemental halogen ($X_2$), which subsequently combines with moisture ($H_2O$) from the ambient environment and disproportionates according to the formula:

$$X_2+2H_2O\rightarrow H^++X^-+HOX$$

resulting in the production of a +1 valent oxidizing species (HOX). Elemental iodine ($I^-$) and hypoiodous acid (HOI), for example, could be formed from an electrolyte containing $I^-$. Alternatively, other anodic reactions can be considered, such as the formation of $H_2O_2$ by the anodic process:

$$H_2O\rightarrow 1/2H_2O_2+H^++e^-$$

The chemical oxidants produced at the positively charged anode (20*a*) can then diffuse to the surface and disinfect by oxidatively reacting with harmful microbes or chemicals, deactivating them or rendering them insoluble. The cathodic (20*b*) reaction involves reduction of oxygen ($O_2$) and moisture from the air to form hydroxide ($OH^-$), as shown in FIG. 2. Charge balance within the electrolyte is maintained since for every halide ion consumed a hydroxide ion is formed. The electrodes may be reversed periodically so that disinfecting oxidants forms at the alternating electrode.

Activation of the electrochemical cell for a substantial period of time may result in depletion of the precursor for the oxidizing agent. However, the cell can easily be regenerated by applying (depositing) a fresh solution of electrolyte containing precursor.

FIG. 3 shows a multilayer electrochemical cell incorporating aspects of the invention. The cell includes a power source (10), two woven non-conducting fabric separators (60) containing electrolyte gel (40), one fabric cathode (70), two fabric anodes (80), and contacts to each anode and cathode via leads (71) and (81) respectively (for simplicity, only one set of leads is shown in FIG. 3). Each non-conducting separator is sandwiched between a cathode and anode, and the side of each electrode in contact with a separator is coated with electrolyte which may penetrate the electrode. This embodiment is flexible and can be easily rolled up or pleated to form an active filter.

The non-conducting, electrolyte-doped fabric (60) could be made from a variety of materials, including without limitation nylon or Teflon. The inner cathode (70) and anodes (80) can be made from porous carbon felt. The carbon felt cathode (70) could be treated with materials such as iodide doped polyanaline in order increase the efficiency of the system by promoting cathodic depolarization.

Although the fabrics shown in FIG. 1 or FIG. 3 are each configured to function as a stand-alone system, these fabrics could alternatively be used as self-decontaminating coatings that provide decontamination, on demand, to a separate surface located adjacent to the fabric.

Figure 4A:
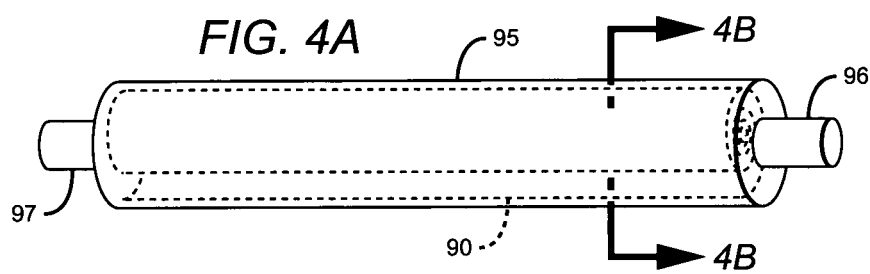
FIG. 4A is a schematic drawing showing an air filtration system incorporating the features of the invention.
Figure 4B:
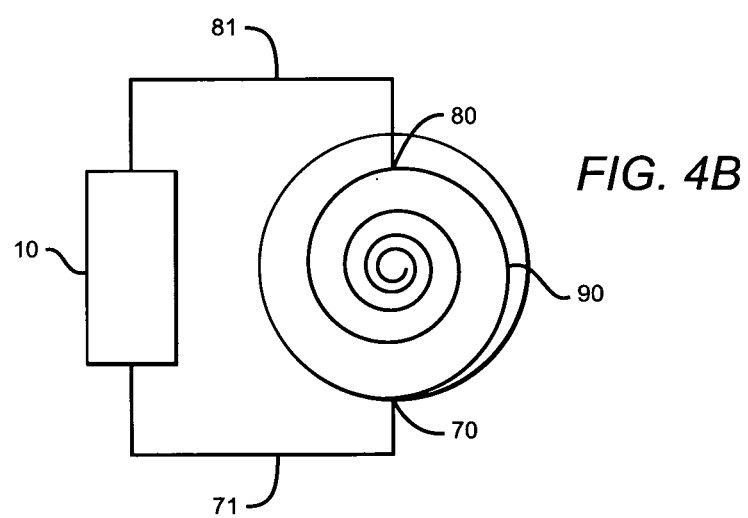
FIG. 4B is a schematic transverse cross section view through the system of FIG. 4A showing the cylindrical shape of the filter.

FIGS. 4A and 4B are schematic diagrams of an air filtration system incorporating features of the invention. The flexible fabric system shown in FIG. 3 can be rolled into a spiral-shaped filter (90) and subsequently contained by a manifold (95) as shown in FIG. 4A. Alternatively the fabric could be folded in an accordion manner and placed in the manifold. The manifold shown in FIG. 4A includes an inlet tube (96) and an outlet tube (97) for the flow of air leading into and out of the manifold (95), respectively.

FIG. 4B is a schematic diagram of a transverse cross section taken through the spiral fabric filter (90) shown in FIG. 4A. As shown in FIG. 4B, the system includes a power source (10), cathode (70), and anode (80). For simplicity, the manifold (95) was omitted from FIG. 4B and the power source (10), cathode (70), and anode (80) components of the system were omitted from FIG. 4A.

Activation of the filter (90) by applying a positive voltage bias of about 3.5 to about 4.0 V on the anode (80), relative to the cathode (70), can generate active oxidizing species in contact with the air stream flowing through the filter. In addition, microbial particulates can become entrapped and oxidized on the outer surface of the spiral roll of filter media (90).

Other types of flexible self-decontaminating fabrics or systems, such as the woven fabric shown in FIG. 1, could also be used. The weave of the fabric may not be fully sealed by the electrolyte gel in this embodiment, but rather deposited as a thin conformal coating over the weave so as to leave some porosity while enabling ionic conductivity between alternating conducting tows.

EXAMPLES

1. Preparation of Gel Electrolytes

The electrolytes were made from ethylene carbonate, propylene carbonate, polyacrylonitrile and a tetrapropylammonium halide where the halide (X) was chloride (Cl), bromide (Br) or iodide (I). The components of each electrolyte were combined in a beaker in proportions by weight according to Table I and heated in a water bath until the solution became homogeneous. The resulting liquid served as the precursor for the solid gelled electrolyte formed between the anode and cathode of the exemplary cells.

TABLE I

GEL ELECTROLYTE COMPOSITIONS

| Compound | $Br^-$ Analog (wt %) | $Cl^-$ Analog (wt %) | $I^-$ Analog (wt %) |
| --- | --- | --- | --- |
| Ethylene carbonate | 33.29 | 33.75 | 32.85 |
| Propylene carbonate | 48.43 | 49.01 | 47.78 |
| polyacrylonitrile | 10.63 | 10.78 | 10.49 |
| Tetrapropylammonium bromide | 7.65 | | |
| Tetrapropylammonium chloride | | 6.46 | |
| Tetrapropylammonium iodide | | | 8.88 |

Example 1

Fabric woven to contain conducting carbon tows alternating with non-conducting nylon tows (see FIG. 1 and FIG. 2) was produced by T.E.A.M. Textiles (Slaterville, R.I.). The woven fabric contained approximately 12 ends per inch of Mitsubishi K13D2U-2K high conductivity carbon pitch tow (800 W/m-K conductor) with separating ends of fine E-glass yarns (estimated pitch approx. 1.5 mm wide bands of conducting tow alternating with 0.5 mm non-conducting tow bands).

Before treating with electrolyte, alternating conducting tows in the fabric were connected to Cu tape electrodes and a voltage between the fibers was slowly ramped up to 100 V, during which time resistive heating (burn in) thermally destroyed spurious shorts between the alternating fibers.

Upon removal of the voltage, a 1.0 inch×2.0 inch (2.5 cm×5.0 cm) or 12.0 inch×12.0 inch (30.5 cm×30.5 cm) portion of the fabric was coated with the chloride electrolyte analog and then laid flat on a non-conducting surface such as a glass backing while the electrolyte gelled. The resulting liquid formed a useable gel within about three days and was completely gelled within about one week.

About 5 to 10 minutes after application of a 4 volt bias across the conducting fibers of the cell, a gas evolved that generated an acid detected by dampened pH paper, indicating the emission of chlorine gas ($Cl_2$).

Example 2

After the proscribed 'burn in', a 1.0 inch×2.0 inch (2.5 cm×5.0 cm) portion of the fabric described in Example 1 was coated with the bromide analog electrolyte (Table 1). The resulting liquid formed a useable gel within about three days and was completely gelled within about a week.

About 10 minutes after application of a 4 volt bias across the fibers of the cell, a liquid formed on the surface of the anodic tow which turned orange-colored fluorescein paper to a pink color, indicating the formation of bromine vapor ($Br_2$).

Example 3

A multilayer electrochemical cell was constructed according to FIG. 3 with two carbon felt anodes and one carbon felt cathode, each of which measured 2 inch×3 inch (5.08 cm×7.62 cm). Non-conducting nylon screens served as the spacers in this cell.

The cathode was prepared by coating a carbon felt cathode with PANI iodide in N-methylpyrrolidine and heating until dried. Polyaniline (PANI) iodide was prepared by reacting a slurry of 3 gm of the oxidized form of PANI (emeraldine base) with an excess of 1M hydriodic acid (HI) for 16 hours followed by separation, washing the residue (PANI iodide) in cold deionized water, and drying the residue. Then 1 gm of the PANI iodide was dissolved in 12 gm N-methyl pyrrolidone using sonication. This solution was applied to a carbon felt and dried for 1 hour at 80-110° C. Coating carbon electrodes with this solution can promote cathodic depolarization.

The cathode was then coated on both sides with the iodide based electrolyte analog described in Table 1, layered on each side with a nylon screen separator, and then sandwiched between two carbon felt porous anodes such that both sides of each separator and the side of each anode in contact with a separator became, like the cathode, coated by or embedded with electrolyte. FIG. 3 is a schematic illustrating the structure of the fabric.

Copper electrodes were then attached to both the cathode and the anodes, as shown schematically in FIG. 3. The electrolyte in the resulting multilayer fabric was allowed to gel for several days, after which the fabric was rolled up and placed in a glass tube. Indicator paper containing 1% starch indicator was placed over the mouth of the tube containing the rolled fabric as air was blown through it. The starch paper showed no color change with the bias off but turned blue when the cell was activated with a 3.5 V bias, indicating the presence of iodine vapor ($I_2$). This result shows that the cloth can inject a disinfecting species into an air stream passing over it.

The embodiments and examples set forth herein were presented to explain the nature of the present invention and its practical application, and thereby to enable those of ordinary skill in the art to make and use the invention. However, those of ordinary skill in the art will recognize that the foregoing description and examples have been presented for the purposes of illustration and example only. The description as set forth is not intended to be exhaustive or to limit the invention to the precise form disclosed. Many modifications and variations are possible in light of the teachings above without departing from the spirit and scope of the forthcoming claims. For example, while the incorporation of halogen salts or compounds which can electrochemically release halogen oxidants is described herein, the invention contemplated is not so limited. One skilled in the art will recognize that other compounds can be used in the same structural arrangement to electrochemically release a decontaminating oxidant, on demand if necessary, including without limitation peroxides, ammonia, permanganates and other known electrochemically-generated oxidizing agents. Similarly, the dimensions, structure, or configuration of other system components may vary and accordingly are not to be construed as limiting the scope of the invention.

We claim:

1. A flexible electrolytic fabric comprising an electrochemical cell, the cell comprising:
   at least two flexible conducting tows or filaments arranged adjacent to each other, and at least one flexible non-conducting tow or filament interwoven with and separating the at least two flexible conducting tows or filaments to form a woven structure, said at least one flexible non-conducting tow or filament electrically isolating said at least two flexible conducting tows or filaments from each other, wherein each adjacent pair of said conducting tows or filaments comprise an anode and a cathode; and
   a hydrophobic electrolyte integral to said fabric and which fills, covers or impregnates said woven structure, said hydrophobic electrolyte comprising at least one precursor for an oxidizing chemical,
   wherein
      the precursor comprises at least one halide ion,
      the oxidizing chemical comprises at least one of a diatomic halogen molecule, a hydroxide ion, an acid having a chemical formula HOX wherein X is a halogen, or a combination thereof, and is effective to substantially remove or devitalize a hazardous biological or chemical agent located at or near the fabric or portion thereof, and
      the electrolyte comprises at least 5 wt % of the precursor, is effective to provide at least one path of ionic conduction between the two conducting tows or filaments, and is chemically stable in the presence of the oxidizing chemical.

2. The fabric of claim 1, the fabric consisting essentially of the electrolyte, the at least two conducting tows, and the at least one non-conducting tow.

3. The fabric of claim 2 wherein the fabric comprises a plurality of adjacent electrochemical cells, each cell comprising two conductive tows, and at two least adjacent cells having a conductive tow in common with each other.

4. The fabric of claim 3 wherein each of substantially all of the conductive tows is part of two adjacent electrochemical cells.

5. The fabric of claim 1, further comprising at least one decontaminating layer not electrically connected to the cell.

6. The fabric of claim 1, wherein the electrolyte is non-aqueous.

7. The fabric of claim 1, wherein the at least one precursor comprises a halide ion.

8. The fabric of claim 1, wherein the fabric comprises at least one porous surface.

9. A decontamination system comprising the fabric of claim 1.

10. A flexible, self-decontaminating device comprising:
   at least one flexible electrolytic fabric comprising an electrochemical cell according to claim 1, the fabric having at least one exposed surface or portion thereof, and an activatable power source electrically connected to the at least one fabric wherein:
   the power source is connected to at least two conducting tows or filaments in the at least one fabric,
   the power source is effective to provide a potential bias between the two conducting tows or filaments so as to create an electron flow through the cell,
   the electron flow is effective to activate the cell and the at least one precursor so as to electrochemically release the oxidizing chemical, and
   the oxidizing chemical is effective to substantially remove or devitalize a hazardous biological or chemical agent located at or near the at least one surface or portion thereof.

11. The device of claim 10 wherein the fabric can be repeatedly positioned in a plurality of shapes, such that it can be repeatedly flattened into a planar configuration and repeatedly rolled into a cylindrical configuration, and the conducting tows are substantially perpendicular to the non-conducting tows, and are substantially parallel to each other when the fabric is in the planar configuration.

12. The device of claim 10, further comprising at least one decontaminating layer wherein the layer is not electrically connected to the cell.

13. The device of claim 10, wherein the electrolyte is nonaqueous.

14. The device of claim 10, wherein the at least one precursor comprises a halide ion.

15. The device of claim 10, wherein the conducting tows are at least one of electrocatalytic and dimensionally stable.

16. The device of claim 10, wherein the fabric is at least one of flexible and resistant to breaks.

17. A decontamination system comprising the device of claim 10.

18. The device of claim 12, wherein at the at least one decontaminating layer is adjacent to the fabric.

19. An electrolytic device comprising:
  at least two conducting tows or filaments arranged adjacent to each other and at least one non-conducting tow or filament interwoven with and separating the at least two conducting tows or filaments to form a woven structure, said at least one flexible non-conducting tow or filament electrically isolating said at least two flexible conducting tows or filaments from each other, wherein each adjacent pair of said conducting tows or filaments comprise an anode and a cathode;
  a hydrophobic electrolyte integral to said device and which fills, covers or impregnates said woven structure, said hydrophobic electrolyte comprising at least one precursor for an oxidizing chemical;
  an activatable power source electrically connected to the at least one device; and
  optionally, at least one decontaminating layer not electrically connected to the cell, wherein
    the power source is connected to anodes and cathodes in the at least one device,
    the precursor comprises at least one halide ion,
    the oxidizing chemical comprises at least one of a diatomic halogen molecule, a hydroxide ion, an acid having a chemical formula HOX wherein X is a halogen, or a combination thereof, and
    the electrolyte comprises at least 5 wt % of the precursor, is effective to provide at least one path of ionic conduction between the two conducting tows or filaments, and is chemically stable in the presence of the oxidizing chemical.

20. A self-decontaminating system comprising at least one electrolytic device according to claim 19, the device having at least one exposed surface or portion thereof, wherein
  the power source is effective to provide a potential bias between the two conducting tows or filaments so as to create an electron flow through the cell,
  the electron flow is effective to activate the cell and the at least one precursor so as to electrochemically release the oxidizing chemical, and
  the oxidizing chemical is effective to substantially remove or devitalize a toxic biological or chemical agent located at or near the at least one surface or portion thereof.

* * * * *